US006815176B1

(12) United States Patent
Zuker et al.

(10) Patent No.: US 6,815,176 B1
(45) Date of Patent: Nov. 9, 2004

(54) ASSAYS FOR SENSORY MODULATORS USING A SENSORY CELL SPECIFIC PHOSPHOLIPASE C

(75) Inventors: Charles S. Zuker, San Diego, CA (US); Jon E. Adler, Pacific Beach, CA (US); Juergen Lindemeier, Werl (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/492,027

(22) Filed: Jan. 26, 2000

Related U.S. Application Data

(60) Provisional application No. 60/117,368, filed on Jan. 27, 1999.

(51) Int. Cl.[7] .................. C12Q 1/44; G01N 33/566; C12N 9/20; C12N 5/00; C12N 15/00
(52) U.S. Cl. .................. 435/19; 435/7.2; 435/198; 435/325; 435/320.1; 435/252.3; 435/69.1; 536/23.2; 530/350
(58) Field of Search .................. 435/198, 19, 325, 435/320.1, 252.3, 69.1, 7.2; 536/23.2; 530/350

(56) References Cited

U.S. PATENT DOCUMENTS 6,329,139 B1 * 12/2001 Nova et al. .................. 435/6

OTHER PUBLICATIONS

Kudo et al., Neuroscience 50:619–725, 1992.*
Bernhardt, etal.: "Changes in $IP_3$ and cytosolic $Ca^2$ in response to sugars and non–sugar sweetners in tranduction of sweet taste in the rat" *Journal of Physiology* (1996) 492.2, pp. 325–336.
Catherine Dulac and Richard Axel: "A Novel Family of Genes Encoding Putative Pheromone Receptors in Mammals" *Cell*, 83 :pp. 195–206.
M.A. Hoon and N.J.P. Ruba: "Analysis and Comparison of Partial Sequences of Clones from a Taste–bud–enriched cDNA Library" *J. Dent Res* 4/97; 76(4) pp. (831–838).
Hoon, etal.: "Putative Mammalian Taste Receptors: A Class of Taste–Specific GPCRs with Distinct Topographic Selectivity" *Cell* Feb. 19, 1999; 96 pp. (541–551).
Jiang, etal.: "Roles of phospholipase C β2 in chemoattractant–elicited responses" *Proc. Natl. Acad Sci.* (7/97); 94 pp. 7971–7975.
Sue C. Kinnamon [1,2] and Robert F. Margolskee [3]: "Mechanisms of taste transduction" *Neurobology* 1996; 6, pp (506–513).
Kusakabe, etal.: "Identification of two α–subunit species of GTP–binding proteins, Gα15 and Gαq, expressed in rat taste buds" *Biochimica et Biophysica Acta* 1998; 1403, pages, (265–272).
McLaughlin, et.al: "Gustducin is a taste–cell specific G protein closely related to the transducins" *Nature* Jun. 18, 1992; 357 pp. 563–569.
Steffan Offermanns and Melvin I. Simon: "$G\alpha_{15}$ and $G\alpha_{16}$ Couple a Wide Variety of Receptors to Phospholipase C*" *Journal of Biological Chemistry* (Jun. 23, 1995) 270:25 pp. 15175–15180.
Park, etal.: "Cloning, Sequencing, Expression, and $G_q$–independent Activation of Phospholipase C–β2*" *Journal of Biological Chemistry* (Aug. 15, 1992), 267:23 pp. 16048–16055.
Rössler, etal: "Identification of a phospholipase C β subtype in rat taste cells" *Journal of Cell Biology* (11/98) 77 pp. 253–261.
Striem, et. al.: "Sweet tastants stimulate adenylate cyclase coupled to GTP–binding protein in rat tongue membranes" *Biochem J.* (1989); 260, pp. 121–126.
Wilke, et. al: "Characterzation of G–protein α subunits in the $G_q$ class: Expression in murine tissues and in stromal and hematopoietic cell lines" *Proc. Natl. Acad. Sci.* 11/91; 88, pp. 10049–10053.
Wong, etal.: "Transduction of bitter and sweet taste by gustducin" *Nature;* (Jun. 27, 1996) 381 pp. 796–800.

* cited by examiner

*Primary Examiner*—Rebecca E. Prouty
*Assistant Examiner*—Delia Ramirez
(74) *Attorney, Agent, or Firm*—Townsend and Townsend and Crew LLP

(57) ABSTRACT

The invention identifies nucleic acid and amino acid sequences of a sensory cell specific phospholipase C that are specifically expressed in taste cells, antibodies to such phospholipase C, methods of detecting such nucleic acids and proteins, and methods of screening for modulators of sensory cell specific phospholipase C.

6 Claims, No Drawings

SEQUENCE LISTING

<160> NUMBER OF SEQ ID NOS: 4

<210> SEQ ID NO 1
<211> LENGTH: 1512
<212> TYPE: DNA
<213> ORGANISM: Rattus sp.
<220> FEATURE:
<223> OTHER INFORMATION: rat taste cell specific phospholipase C beta2
      (TC-PLCbeta2) (165-170 clone)

<400> SEQUENCE: 1

```
gccatgtgag cccagcctag cttcccctcc agttcaccct ccttccttct ctcctcctgt      60
ccactggaga ggtttgccca acctctgcaa agagggacaa ttgacatcat gtctttgctc     120
aaccctgtcc tgttgccccc taaggtgaag gcatatctga gccaagggga gcgcttcatc     180
aagtgggacg atgaaacctc aatagcctcc cctgttatcc ttcgggtgga tcccaagggc     240
tattacttat actggacaca tcaaagtaag gagatggaat ttctggatgt cacgagcatc     300
cgagacactc gctttgggaa gtttgccaag atacccaaga gccagaaact ccgggaggta     360
ttcaacatgg actttccaga caaccacttc ctgctgaaaa cattcacagt ggtatccggc     420
ccggacatgg tgggcctcac cttccacaat tttgtctctt acaaggagaa cgtaggcaag     480
gattgggctg aggatgtact ggctctggcc aaacacccaa tgcagccaa tgcttctcga     540 agcacattcc tagacaagat cctggtgaag cttaaaatgc agctgagccc tgaagggaag     600
atccctgtga agaattttt ccagatgttt cctgccgatc gcaaacgtgt agaagctgcc     660
ctcagtgcct gtcaccttgc aaaaggcaag aatgatgcta tcaatcccga ggacttccca     720
gaatctgtgt acaagagctt cctcatgagc ctctgtcctc ggccagaaat tgatgagatc     780
ttcacttctt atcatgctaa agccaaaccc tacatgacca aggagcacct gaccaaattc     840
atcaatcaga agcaacgaga ccctcgactc aattccttgc tgttcccacc agcccggcct     900
gagcaggtgc aggcgctcat tgacaagtac gagcccagcg gcatcaatgt gcagaggggc     960
caactgtcac cagagggcat ggtctggttt ctctgtggac cagagaacag tgtcctggcc    1020
catgatactc tgcggatcca ccaagacatg acacagcctc tgaatcacta cttcatcaac    1080
tcctcacaca cacctacct gacagctggc cagttttcag gcccttcctc ggctgagatg    1140
taccgccagg tgctgctatc tggctgccgt tgtgtagaat tagattgttg gaaaggaaag    1200
ccccccgacg aagaacccat catcacccac ggcttcacta tgaccacaga tatcttgttc    1260
aaggaagcag tcgaagccat tgcagaaagt gcctttaaga cctccccata tcctgtcatc    1320
ctgtcatttg aaaaccacgt ggactcaccc cgccaacagg ctaagatggc cgagtactgc    1380
cggaccatgt ttggagagac cttgctcaca gagcccctgg aaaactttcc tctgaaacct    1440
ggcatgcctc tgcctagccc tgaggacctc cggggcaaga tcctcattaa gaataagaag    1500
aaccagtttt ct                                                        1512
```

<210> SEQ ID NO 2
<211> LENGTH: 456
<212> TYPE: PRT
<213> ORGANISM: Rattus sp.

```
<220> FEATURE:
<223> OTHER INFORMATION: rat taste cell specific phospholipase C beta 2
      (TC-PLCbeta2) (165-170 clone)

<400> SEQUENCE: 2

Ala Tyr Leu Ser Gln Gly Glu Arg Phe Ile Lys Trp Asp Asp Glu Thr
 1               5                  10                  15

Ser Ile Ala Ser Pro Val Ile Leu Arg Val Asp Pro Lys Gly Tyr Tyr
             20                  25                  30

Leu Tyr Trp Thr His Gln Ser Lys Glu Met Glu Phe Leu Asp Val Thr
         35                  40                  45

Ser Ile Arg Asp Thr Arg Phe Gly Lys Phe Ala Lys Ile Pro Lys Ser
 50                  55                  60

Gln Lys Leu Arg Glu Val Phe Asn Met Asp Phe Pro Asp Asn His Phe
 65                  70                  75                  80

Leu Leu Lys Thr Phe Thr Val Ser Gly Pro Asp Met Val Gly Leu
                 85                  90                  95

Thr Phe His Asn Phe Val Ser Tyr Lys Glu Asn Val Gly Lys Asp Trp
                100                 105                 110

Ala Glu Asp Val Leu Ala Leu Ala Lys His Pro Met Thr Ala Asn Ala
            115                 120                 125

Ser Arg Ser Thr Phe Leu Asp Lys Ile Leu Val Lys Leu Lys Met Gln
130                 135                 140

Leu Ser Pro Glu Gly Lys Ile Pro Val Lys Asn Phe Gln Met Phe
145                 150                 155                 160

Pro Ala Asp Arg Lys Arg Val Glu Ala Ala Leu Ser Ala Cys His Leu
                165                 170                 175

Ala Lys Gly Lys Asn Asp Ala Ile Asn Pro Glu Asp Phe Pro Glu Ser
            180                 185                 190

Val Tyr Lys Ser Phe Leu Met Ser Leu Cys Pro Arg Pro Glu Ile Asp
        195                 200                 205

Glu Ile Phe Thr Ser Tyr His Ala Lys Ala Lys Pro Tyr Met Thr Lys
210                 215                 220

Glu His Leu Thr Lys Phe Ile Asn Gln Lys Gln Arg Asp Pro Arg Leu
225                 230                 235                 240

Asn Ser Leu Leu Phe Pro Pro Ala Arg Pro Glu Gln Val Gln Ala Leu
                245                 250                 255

Ile Asp Lys Tyr Glu Pro Ser Gly Ile Asn Val Gln Arg Gly Gln Leu
            260                 265                 270

Ser Pro Glu Gly Met Val Trp Phe Leu Cys Gly Pro Glu Asn Ser Val
        275                 280                 285

Leu Ala His Asp Thr Leu Arg Ile His Gln Asp Met Thr Gln Pro Leu
290                 295                 300

Asn His Tyr Phe Ile Asn Ser Ser His Asn Thr Tyr Leu Thr Ala Gly
305                 310                 315                 320

Gln Phe Ser Gly Pro Ser Ser Ala Glu Met Tyr Arg Gln Val Leu Leu
                325                 330                 335

Ser Gly Cys Arg Cys Val Glu Leu Asp Cys Trp Lys Gly Lys Pro Pro
            340                 345                 350

Asp Glu Glu Pro Ile Ile Thr His Gly Phe Thr Met Thr Thr Asp Ile
        355                 360                 365

Leu Phe Lys Glu Ala Val Glu Ala Ile Ala Glu Ser Ala Phe Lys Thr
370                 375                 380

Ser Pro Tyr Pro Val Ile Leu Ser Phe Glu Asn His Val Asp Ser Pro
```

-continued

```
            385                 390                 395                 400
Arg Gln Gln Ala Lys Met Ala Glu Tyr Cys Arg Thr Met Phe Gly Glu
                405                 410                 415

Thr Leu Leu Thr Glu Pro Leu Glu Asn Phe Pro Leu Lys Pro Gly Met
            420                 425                 430

Pro Leu Pro Ser Pro Glu Asp Leu Arg Gly Lys Ile Leu Ile Lys Asn
        435                 440                 445

Lys Lys Asn Gln Phe Ser Gly Pro
    450                 455
```

<210> SEQ ID NO 3
<211> LENGTH: 4519
<212> TYPE: DNA
<213> ORGANISM: Homo sapiens
<220> FEATURE:
<223> OTHER INFORMATION: human taste cell specific phospholipase C beta2 (TC-PLCbeta 2)

<400> SEQUENCE: 3

| | | | | | |
|---|---|---|---|---|---|
| cagccagggc | cacccagggg | gctataagag | caactagatt | tctggagcag | ctcggggatg | 60 |
| ggtgccattt | gagcccagct | tggctccccc | tcctggctgg | cctccttcct | gcccttctgc | 120 |
| ctgcctgtgt | ctgctgagat | tctgcaaaga | ggaacgttgg | caccatgtct | ctgctcaacc | 180 |
| ctgtcctgct | gccccccaag | gtgaaggcct | atctgagcca | aggggagcgc | ttcatcaaat | 240 |
| gggatgatga | aactacagtt | gcctctccag | ttatcctccg | tgtggatcct | aagggctact | 300 |
| acttatactg | gacgtatcaa | agtaaggaga | tggagtttct | ggatatcacc | agcatccggg | 360 |
| atactcgctt | tgggaagttt | gccaagatgc | ccaagagcca | gaagctccgg | gacgtcttca | 420 |
| acatggactt | tcctgataac | agttttcctgc | tgaagacact | cacggtggtg | tccggcccgg | 480 |
| acatggtgga | cctcaccttc | cacaacttcg | tctcctacaa | ggagaacgtg | ggcaaggcct | 540 |
| gggctgagga | cgtactggcc | ctagtcaaac | atccgctgac | ggccaacgcc | tcccgcagca | 600 |
| ccttcctgga | caagatcctt | gtgaagctca | agatgcagct | caactctgaa | gggaagattc | 660 |
| cggtgaagaa | cttttttccag | atgtttcctg | ctgaccgcaa | gcgggtggaa | gctgctctca | 720 |
| gtgcctgcca | cctcccaaa | ggcaaaaatg | acgccatcaa | tcctgaggac | ttcccagaac | 780 |
| ctgtctacaa | gagtttcctc | atgagcctct | gtcctcggcc | agaaatagat | gagatcttca | 840 |
| cttcttacca | tgctaaggcc | aaaccctaca | tgacgaagga | gcacctgacc | aaattcatca | 900 |
| accagaaaca | gcgggactcc | cggcttaact | ccctgctgtt | cccgccagca | cggcctgacc | 960 |
| aggtgcaggg | cctcatcgac | aagtatgagc | ccagtggcat | caatgcacag | aggggccagc | 1020 |
| tgtcacctga | aggcatggtc | tggttttctct | gtgggccaga | aacagcgtg | ctggcccagg | 1080 |
| acaagctgct | gctccaccac | gacatgacgc | agccactcaa | tcattacttc | atcaactcgt | 1140 |
| cccacaacac | ctacctgaca | gccggccagt | tctcaggcct | ctcctcggct | gagatgtacc | 1200 |
| gccaggtgct | gctctctggc | tgccgttgcg | tggagctaga | ctgctggaag | gggaaacccc | 1260 |
| ctgacgagga | gccattatc | acccatggct | tcaccatgac | cacagacatc | ttcttcaaag | 1320 |
| aagcaattga | ggctattgca | gaaagtgcct | ttaagacctc | ccctatccc | atcatcctgt | 1380 |
| cgtttgagaa | ccatgtggac | tcaccccgc | agcaggctaa | gatggctgag | tattgccgga | 1440 |
| cgatctttgg | ggatatgctg | ctcacagagc | ccctggaaaa | gttcccacta | aaaccaggtg | 1500 |
| tccccctgcc | cagccctgag | gatctcaggg | gcaagatcct | catcaagaac | aagaagaacc | 1560 |
| agttttctgg | ccccacctcc | tccagtaagg | ataccggtgg | ggaggctgag | ggcagcagcc | 1620 |

-continued

```
cacccagtgc ccctgcagtg tgggctggcg aggaagggac tgagctggag gaggaggagg   1680
tggaagagga agaggaggag gagtcaggaa acctggatga agaagagatt aagaagatgc   1740
agtcggatga gggcacagcg ggcctggaag tgacggctta tgaggagatg tccagcctag   1800
tcaattacat ccagcccacc aagttcgtct cctttgagtt ctctgccaa aagaaccgaa    1860
gttatgtcat ctcgtccttc acagagctca aggcatatga cctgctctcc aaggcctcgg   1920
tgcagtttgt ggactacaac aagcgccaga tgagccgcat ttaccccaag ggaacccgca   1980
tggactcctc caactacatg ccccagatgt tctggaatgc tggatgccag atggttgccc   2040
tcaacttcca gacgatggac ttgcccatgc agcagaacat ggcagtattt gagttcaacg   2100
ggcagagcgg ctacctcctc aagcatgagt tcatgcgccg gccggacaag cagttcaacc   2160
ccttctcagt ggaccgcatc gacgtggtgg tggccaccac cctttccatt acggtgatct   2220
ctgggcagtt cctgtcagaa cgcagcgtgc gcacctatgt agaagtggag ctgtttggcc   2280
ttcctgggga ccccaagagg cgctatcgaa ctaagctgtc acccagtact aactccatca   2340
atcctgtctg gaaggaggag cccttttgtct ttgagaagat cttgatgcct gagctggcct   2400
ccctcagagt ggctgtgatg gaggaaggca acaagtttct tggacaccgc atcatcccca   2460
tcaatgccct aaattctggg taccaccacc tgtgcctgca cagtgagagc aacatgcccc   2520
tcaccatgcc tgcgctcttc atcttcctgg agatgaagga ctacatacct ggtgcttggg   2580
cagatctcac tgtggccctc gccaaccca ttaagttctt cagtgcccat gacacgaagt    2640
ctgtgaagct caaggaggcc atgggaggtc tgcctgagaa gcccttccca ctggcgagtc   2700
cagttgccag ccaggtcaat ggggcgttgg ccccaacgag caatgggtca ccagcagcca   2760
gggccgggc cagggaagag gctatgaaag aagctgcgga ccgcggacc gcagcctgg     2820
aggagctccg ggagctaaag ggcgtggtga agctgcagcg gcggcacgag aaggagctgc   2880
gagagttgga gcggcgcgga gcgcggcgct gggaggagct gctgcagcgg ggcgcggcgc   2940
agctggcgga gctcgggcca ccgggcgtgg ggggcgtcgg ggcctgcaag ctcggtcccg   3000
gcaagggctc tcgcaagaag aggagcctgc cccgcgagga gagcgccgga gccgcgccgg   3060
gcgagggccc tgagggcgtg gacgggcgcg tgcgggagct gaaagacagg ctggagctgg   3120
agctgctgcg gcagggcgag gagcagtacg agtgcgttct gaagcgcaag gagcagcacg   3180
tggccgagca aatctccaaa atgatggagc tggccagaga gaaacaggcg gcagagctga   3240
aggccctgaa ggagacgtcg gagaacgaca ccaaagagat gaagaaaaag ctggagacaa   3300
agagactgga gcggatccag ggcatgacca agtcaccac agacaagatg gcccaggaga    3360
ggttgaagag agagattaac aactcccaca tccaggaagt agtgcaggtg atcaagcaga   3420
tgacggagaa cttggagagg caccaggaga agctggagga gaagcaggcg gcttgcctgg   3480
aacagatacg ggagatggaa aagcagttcc agaaggaggc gctggcagag tacgaggcca   3540
ggatgaaggg tctggaggca gaggtgaagg agtcggtgag ggcctgcctc aggacctgct   3600
ttccctccga ggccaaggac aagcctgaga gggcctgcga gtgcccccca gagctgtgtg   3660
agcaggacca actcatagca aaggcagatg cccaggagag ccgcctctga tgcccccatc   3720
ccactgggac atttagcaag gaggttcagc cccttctctg ggatgtggtt ctattccccc   3780
aggaaaaagg agcccagcc ttctgaggct gtgggaacct gtggctgcct ggacgctgc    3840
agccccctcc tcaacggcca ggccagagtc tgagacagga cccaggcacc ctcacggcag   3900
ggcctctctg gggcctagaa gtcttctcaa gctgacttcc tacctccccc tccatctcta   3960
gataagtgtc atatatttgt tgagggcaaa agactatgga ctggaaggca gaaagtggga   4020
```

-continued

```
tcctggcccc actctgcctt tcctattgag caaccagctc tgggctcagt ttcctcacct    4080
ggagggttgg acccactcac ctccactcta gccccgaacc ctcctgcccc aggcttccag    4140
gccccatcag gcctgccctg agttggcctt gtccactcct tgaggcagat cctggcacta    4200
cctcacagct ccctggggac ggccactccc tggctgaggg ccctcccctc ccctctgcct    4260
gtccggaacg ggaggctgaa atggaaaagc tgccttggcc ctgcttggct gagtcacaag    4320
gggcagtggg ctcttgggtg ctgttccacc ctgaccctgg ctcacccctc ttcctaggcc    4380
tgggggcagg cagttcctac catgtacccc tctcaggctg cctgcctgac aaggtcagca    4440
tcatttgctc tcctgaattt atgaggttta tttattttc tctttcctac tcctattaaa    4500
gaacctcgtc ccagtgaaa                                                 4519

<210> SEQ ID NO 4
<211> LENGTH: 1181
<212> TYPE: PRT
<213> ORGANISM: Homo sapiens
<220> FEATURE:
<223> OTHER INFORMATION: human taste cell specific phospholipase C beta2
      (TC-PLCbeta2)

<400> SEQUENCE: 4

Met Ser Leu Leu Asn Pro Val Leu Leu Pro Pro Lys Val Lys Ala Tyr
  1               5                  10                  15

Leu Ser Gln Gly Glu Arg Phe Ile Lys Trp Asp Asp Glu Thr Thr Val
                 20                  25                  30

Ala Ser Pro Val Ile Leu Arg Val Asp Pro Lys Gly Tyr Tyr Leu Tyr
             35                  40                  45

Trp Thr Tyr Gln Ser Lys Glu Met Glu Phe Leu Asp Ile Thr Ser Ile
         50                  55                  60

Arg Asp Thr Arg Phe Gly Lys Phe Ala Lys Met Pro Lys Ser Gln Lys
 65                  70                  75                  80

Leu Arg Asp Val Phe Asn Met Asp Phe Pro Asp Asn Ser Phe Leu Leu
                 85                  90                  95

Lys Thr Leu Thr Val Val Ser Gly Pro Asp Met Val Asp Leu Thr Phe
            100                 105                 110

His Asn Phe Val Ser Tyr Lys Glu Asn Val Gly Lys Ala Trp Ala Glu
        115                 120                 125

Asp Val Leu Ala Leu Val Lys His Pro Leu Thr Ala Asn Ala Ser Arg
    130                 135                 140

Ser Thr Phe Leu Asp Lys Ile Leu Val Lys Leu Lys Met Gln Leu Asn
145                 150                 155                 160

Ser Glu Gly Lys Ile Pro Val Lys Asn Phe Phe Gln Met Phe Pro Ala
                165                 170                 175

Asp Arg Lys Arg Val Glu Ala Ala Leu Ser Ala Cys His Leu Pro Lys
            180                 185                 190

Gly Lys Asn Asp Ala Ile Asn Pro Glu Asp Phe Pro Glu Pro Val Tyr
        195                 200                 205

Lys Ser Phe Leu Met Ser Leu Cys Pro Arg Pro Glu Ile Asp Glu Ile
    210                 215                 220

Phe Thr Ser Tyr His Ala Lys Ala Lys Pro Tyr Met Thr Lys Glu His
225                 230                 235                 240

Leu Thr Lys Phe Ile Asn Gln Lys Gln Arg Asp Ser Arg Leu Asn Ser
                245                 250                 255

Leu Leu Phe Pro Pro Ala Arg Pro Asp Gln Val Gln Gly Leu Ile Asp
```

-continued

```
                260                 265                 270
Lys Tyr Glu Pro Ser Gly Ile Asn Ala Gln Arg Gly Gln Leu Ser Pro
            275                 280                 285
Glu Gly Met Val Trp Phe Leu Cys Gly Pro Glu Asn Ser Val Leu Ala
        290                 295                 300
Gln Asp Lys Leu Leu Leu His His Asp Met Thr Gln Pro Leu Asn His
305                 310                 315                 320
Tyr Phe Ile Asn Ser Ser His Asn Thr Tyr Leu Thr Ala Gly Gln Phe
                325                 330                 335
Ser Gly Leu Ser Ser Ala Glu Met Tyr Arg Gln Val Leu Leu Ser Gly
            340                 345                 350
Cys Arg Cys Val Glu Leu Asp Cys Trp Lys Gly Lys Pro Pro Asp Glu
        355                 360                 365
Glu Pro Ile Ile Thr His Gly Phe Thr Met Thr Thr Asp Ile Phe Phe
        370                 375                 380
Lys Glu Ala Ile Glu Ala Ile Ala Glu Ser Ala Phe Lys Thr Ser Pro
385                 390                 395                 400
Tyr Pro Ile Ile Leu Ser Phe Glu Asn His Val Asp Ser Pro Arg Gln
                405                 410                 415
Gln Ala Lys Met Ala Glu Tyr Cys Arg Thr Ile Phe Gly Asp Met Leu
            420                 425                 430
Leu Thr Glu Pro Leu Glu Lys Phe Pro Leu Lys Pro Gly Val Pro Leu
        435                 440                 445
Pro Ser Pro Glu Asp Leu Arg Gly Lys Ile Leu Ile Lys Asn Lys Lys
        450                 455                 460
Asn Gln Phe Ser Gly Pro Thr Ser Ser Ser Lys Asp Thr Gly Gly Glu
465                 470                 475                 480
Ala Glu Gly Ser Ser Pro Ser Ala Pro Ala Val Trp Ala Gly Glu
            485                 490                 495
Glu Gly Thr Glu Leu Glu Glu Glu Val Glu Glu Glu Glu Glu
        500                 505                 510
Glu Ser Gly Asn Leu Asp Glu Glu Ile Lys Lys Met Gln Ser Asp
        515                 520                 525
Glu Gly Thr Ala Gly Leu Glu Val Thr Ala Tyr Glu Glu Met Ser Ser
        530                 535                 540
Leu Val Asn Tyr Ile Gln Pro Thr Lys Phe Val Ser Phe Glu Phe Ser
545                 550                 555                 560
Ala Gln Lys Asn Arg Ser Tyr Val Ile Ser Ser Phe Thr Glu Leu Lys
            565                 570                 575
Ala Tyr Asp Leu Leu Ser Lys Ala Ser Val Gln Phe Val Asp Tyr Asn
            580                 585                 590
Lys Arg Gln Met Ser Arg Ile Tyr Pro Lys Gly Thr Arg Met Asp Ser
        595                 600                 605
Ser Asn Tyr Met Pro Gln Met Phe Trp Asn Ala Gly Cys Gln Met Val
        610                 615                 620
Ala Leu Asn Phe Gln Thr Met Asp Leu Pro Met Gln Gln Asn Met Ala
625                 630                 635                 640
Val Phe Glu Phe Asn Gly Gln Ser Gly Tyr Leu Leu Lys His Glu Phe
                645                 650                 655
Met Arg Arg Pro Asp Lys Gln Phe Asn Pro Phe Ser Val Asp Arg Ile
            660                 665                 670
Asp Val Val Val Ala Thr Thr Leu Ser Ile Thr Val Ile Ser Gly Gln
        675                 680                 685
```

```
Phe Leu Ser Glu Arg Ser Val Arg Thr Tyr Val Glu Val Leu Phe
    690                 695                 700
Gly Leu Pro Gly Asp Pro Lys Arg Arg Tyr Arg Thr Lys Leu Ser Pro
705                 710                 715                 720
Ser Thr Asn Ser Ile Asn Pro Val Trp Lys Glu Pro Phe Val Phe
                725                 730                 735
Glu Lys Ile Leu Met Pro Glu Leu Ala Ser Leu Arg Val Ala Val Met
                740                 745                 750
Glu Glu Gly Asn Lys Phe Leu Gly His Arg Ile Ile Pro Ile Asn Ala
            755                 760                 765
Leu Asn Ser Gly Tyr His His Leu Cys Leu His Ser Glu Ser Asn Met
770                 775                 780
Pro Leu Thr Met Pro Ala Leu Phe Ile Phe Leu Glu Met Lys Asp Tyr
785                 790                 795                 800
Ile Pro Gly Ala Trp Ala Asp Leu Thr Val Ala Leu Ala Asn Pro Ile
                805                 810                 815
Lys Phe Phe Ser Ala His Asp Thr Lys Ser Val Lys Leu Lys Glu Ala
                820                 825                 830
Met Gly Gly Leu Pro Glu Lys Pro Phe Pro Leu Ala Ser Pro Val Ala
                835                 840                 845
Ser Gln Val Asn Gly Ala Leu Ala Pro Thr Ser Asn Gly Ser Pro Ala
850                 855                 860
Ala Arg Ala Gly Ala Arg Glu Glu Ala Met Lys Glu Ala Ala Glu Pro
865                 870                 875                 880
Arg Thr Ala Ser Leu Glu Glu Leu Arg Glu Leu Lys Gly Val Val Lys
                885                 890                 895
Leu Gln Arg Arg His Glu Lys Glu Leu Arg Glu Leu Glu Arg Arg Gly
                900                 905                 910
Ala Arg Arg Trp Glu Glu Leu Leu Gln Arg Gly Ala Ala Gln Leu Ala
                915                 920                 925
Glu Leu Gly Pro Pro Gly Val Gly Gly Val Gly Ala Cys Lys Leu Gly
            930                 935                 940
Pro Gly Lys Gly Ser Arg Lys Lys Arg Ser Leu Pro Arg Glu Glu Ser
945                 950                 955                 960
Ala Gly Ala Ala Pro Gly Glu Gly Pro Glu Gly Val Asp Gly Arg Val
                965                 970                 975
Arg Glu Leu Lys Asp Arg Leu Glu Leu Glu Leu Leu Arg Gln Gly Glu
                980                 985                 990
Glu Gln Tyr Glu Cys Val Leu Lys Arg Lys Glu Gln His Val Ala Glu
            995                 1000                1005
Gln Ile Ser Lys Met Met Glu Leu Ala Arg Glu Lys Gln Ala Ala Glu
    1010                1015                1020
Leu Lys Ala Leu Lys Glu Thr Ser Glu Asn Asp Thr Lys Glu Met Lys
1025                1030                1035                1040
Lys Lys Leu Glu Thr Lys Arg Leu Glu Arg Ile Gln Gly Met Thr Lys
                1045                1050                1055
Val Thr Thr Asp Lys Met Ala Gln Glu Arg Leu Lys Arg Glu Ile Asn
                1060                1065                1070
Asn Ser His Ile Gln Glu Val Val Gln Val Ile Lys Gln Met Thr Glu
            1075                1080                1085
Asn Leu Glu Arg His Gln Glu Lys Leu Glu Glu Lys Gln Ala Ala Cys
    1090                1095                1100
```

-continued

```
Leu Glu Gln Ile Arg Glu Met Glu Lys Gln Phe Gln Lys Glu Ala Leu
1105                1110                1115                1120

Ala Glu Tyr Glu Ala Arg Met Lys Gly Leu Glu Ala Glu Val Lys Glu
            1125                1130                1135

Ser Val Arg Ala Cys Leu Arg Thr Cys Phe Pro Ser Glu Ala Lys Asp
            1140                1145                1150

Lys Pro Glu Arg Ala Cys Glu Cys Pro Pro Glu Leu Cys Glu Gln Asp
        1155                1160                1165

Pro Leu Ile Ala Lys Ala Asp Ala Gln Glu Ser Arg Leu
    1170                1175                1180
```

ASSAYS FOR SENSORY MODULATORS USING A SENSORY CELL SPECIFIC PHOSPHOLIPASE C

CROSS-REFERENCES TO RELATED APPLICATIONS

This application claims priority to U.S. Ser. No. 60/117,368, filed Jan. 27, 1999, the disclosure of which is herein incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant No. DC03160, awarded by the National Institutes of Health. The Government has certain rights in this invention.

FIELD OF THE INVENTION

The invention identifies nucleic acid and amino acid sequences of a sensory cell specific phospholipase C that are specifically expressed in taste cells, antibodies to such phospholipase C, methods of detecting such nucleic acids and proteins, and methods of screening for modulators of sensory cell specific phospholipase C.

BACKGROUND OF THE INVENTION

Taste transduction is one of the most sophisticated forms of chemotransduction in animals (see, e.g., Avenet & Lindemann, J. Membrane Biol. 112:1–8 (1989); Margolskee, BioEssays 15:645–650 (1993)). Gustatory signaling is found throughout the animal kingdom, from simple metazoans to the most complex of vertebrates; its main purpose is to provide a reliable signaling response to non-volatile ligands. Higher organisms have four basic types of taste modalities: salty, sour, sweet, and bitter. Each of these modalities is thought to be mediated by distinct signaling pathways leading to receptor cell depolarization, generation of a receptor or action potential, and the release of neurotransmitter and synaptic activity (see, e.g., Roper, Ann. Rev. Neurosci. 12:329–353 (1989)).

Mammals are believed to have five basic taste modalities: sweet, bitter, sour, salty and unami (the taste of monosodium glutamate) (see, e.g., Kawamura & Kare, Introduction to Umami: A Basic Taste (1987); Kinnamon & Cummings, Ann. Rev. Physiol. 54:715–731(1992); Lindemann, Physiol. Rev. 76:718–766 (1996); Stewart et al., Am. J Physiol. 272:1–26 (1997)). Extensive psychophysical studies in humans have reported that different regions of the tongue display different gustatory preferences (see, e.g., Hoffmann, Menchen. Arch. Path. Anat. Physiol. 62:516–530 (1875); Bradley et al., Anatomical Record 212: 246–249 (1985); Miller & Reedy, Physiol. Behav. 47:1213–1219 (1990)). Also, numerous physiological studies in animals have shown that taste receptor cells may selectively respond to different tastants (see, e.g., Akabas et al., Science 242:1047–1050 (1988); Gilbertson et al., J. Gen. Physiol. 100:803–24 (1992); Bernhardt et al., J. Physiol. 490:325–336 (1996); Cummings et al., J. Neurophysiol. 75:1256–1263 (1996)).

In mammals, taste receptor cells are assembled into taste buds that are distributed into different papillae in the tongue epithelium. Circumvallate papillae, found at the very back of the tongue, contain hundreds (mice) to thousands (human) of taste buds and are particularly sensitive to bitter substances. Foliate papillae, localized to the posterior lateral edge of the tongue, contain dozens to hundreds of taste buds and are particularly sensitive to sour and bitter substances. Fungiform papillae containing a single or a few taste buds are at the front of the tongue and are thought to mediate much of the sweet taste modality.

Each taste bud, depending on the species, contain 50–150 cells, including precursor cells, support cells, and taste receptor cells (see, e.g., Lindemann, Physiol. Rev. 76:718–766 (1996)). Receptor cells are innervated at their base by afferent nerve endings that transmit information to the taste centers of the cortex through synapses in the brain stem and thalamus. Elucidating the mechanisms of taste cell signaling and information processing are critical for understanding the function, regulation, and "perception" of the sense of taste.

Although much is known about the psychophysics and physiology of taste cell function, very little is known about the molecules and pathways that mediate these sensory signaling responses (reviewed by Gilbertson, Current Opn. in Neurobiol. 3:532–539 (1993)). Electrophysiological studies suggest that sour and salty tastants modulate taste cell function by direct entry of $H^+$ and $Na^+$ ions through specialized membrane channels on the apical surface of the cell. In the case of sour compounds, taste cell depolarization is hypothesized to result from $H^+$ blockage of $K^+$ channels (see, e.g., Kinnamon et al., PNAS USA 85: 7023–7027 (1988)) or activation of pH-sensitive channels (see, e.g., Gilbertson et al., J. Gen. Physiol. 100:803–24 (1992)); salt transduction may be partly mediated by the entry of $Na^+$ via amiloride-sensitive $Na^+$ channels (see, e.g., Heck et al., Science 223:403–405 (1984); Brand et al., Brain Res. 207–214 (1985); Avenet et al., Nature 331: 351–354 (1988)). Most of molecular components of the sour or salty pathways have not been identified.

Sweet, bitter, and unami transduction are believed to be mediated by G-protein-coupled receptor (GPCR) signaling pathways (see, e.g., Striem et al., Biochem. J. 260:121–126 (1989); Chaudhari et al., J. Neuros. 16:3817–3826 (1996); Wong et al., Nature 381: 796–800 (1996)). Confusingly, there are almost as many models of signaling pathways for sweet and bitter transduction as there are effector enzymes for GPCR cascades (e.g., G protein subunits, cGMP phosphodiesterase, phospholipase C, adenylate cyclase; see, e.g., Kinnamon & Margolskee, Curr. Opin. Neurobiol. 6:506–513 (1996)). Identification of molecules involved in taste signaling is important given the numerous pharmacological and food industry applications for bitter antagonists, sweet agonists, and modulators of salty and sour taste.

The identification and isolation of taste receptors (including taste ion channels), and taste signaling molecules, such as G-protein subunits and enzymes involved in signal transduction, would allow for the pharmacological and genetic modulation of taste transduction pathways. For example, availability of receptor, ion channels, and other molecules involved in taste transduction would permit the screening for high affinity agonists, antagonists, inverse agonists, and modulators of taste cell activity. Such taste modulating compounds could then be used in the pharmaceutical and food industries to customize taste. In addition, such taste cell specific molecules can serve as invaluable tools in the generation of taste topographic maps that elucidate the relationship between the taste cells of the tongue and taste sensory neurons leading to taste centers in the brain.

SUMMARY OF THE INVENTION

The present invention demonstrates, for the first time, taste cell specific expression of nucleic acid encoding phospholipase C beta 2. Phospholipase C plays a central role in transmembrane signaling by catalyzing the hydrolysis of phosphatidylinositol 4,5-biphosphate and generating second messenger molecules involved in signal transduction in cells. The phospholipase Cs that are specifically expressed in taste cells are involved in the taste transduction pathway, and can thus be used to screen for modulators of taste. The compounds identified in these assays would then be used by the food and pharmaceutical industries to customize taste, e.g., as addition to food or medicine so that the food or medicine tastes different to the subject who ingests it. For example, bitter medicines can be made to taste less bitter, and sweet substance can be enhanced.

In one aspect, the present invention provides a method for identifying a compound that modulates sensory signaling in sensory cells, the method comprising the steps of: (i) contacting the compound with a sensory specific phospholipase C, the phospholipase C comprising greater than 70% amino acid sequence identity to an amino acid sequence of SEQ ID NO:2 or SEQ ID NO:4; and (ii) determining the functional effect of the compound upon the phospholipase C.

In one embodiment, the phospholipase C specifically binds to polyclonal antibodies generated against SEQ ID NO:2 or SEQ ID NO:4.

In another embodiment, the functional effect is a chemical effect.

In another embodiment, the functional effect is a physical effect.

In another embodiment, the functional effect is determined by measuring changes in intracellular cAMP, cGMP, $IP_3$, DAG, or $Ca^{2+}$.

In another embodiment, the phospholipase C is expressed in a cell. In another embodiment, the phospholipase C is expressed in a eukaryotic cell.

In another embodiment, the functional effect is determined by measuring changes in the electrical activity of the cell expressing the phospholipase C.

In another embodiment, the changes in the electrical activity are measured by an assay selected from the group consisting of a voltage clamp assay, a patch clamp assay, a radiolabeled ion flux assay, and a fluorescence assay using voltage sensitive dyes.

In another embodiment, the functional effect is determined by measuring changes in the level of phosphorylation of taste cell specific proteins.

In another embodiment, the functional effect is determined by measuring changes in transcription levels of taste cell specific genes.

In another embodiment, the phospholipase C is linked to a solid phase.

In another embodiment, the phospholipase C is covalently linked to a solid phase.

In another embodiment, the phospholipase Cs are recombinant.

In another embodiment, the phospholipase C is from a human, a mouse or a rat.

In another embodiment, the phospholipase Cs have an amino acid sequence of SEQ ID NO:2 or SEQ ID NO:4.

In another aspect, the present invention provides a method identifying a compound that modulates sensory signaling in sensory cells, the method comprising the steps of: (i) expressing a sensory cell specific phospholipase C in a host cell, wherein the phospholipase C has greater than 70% amino acid sequence identity to a polypeptide having a sequence of SEQ ID NO:2 or SEQ ID NO:4; (ii) expressing a promiscuous G-protein alpha polypeptide and a taste cell specific G-protein coupled receptor in the host cell, (iii) contacting the host cell with the compound that modulates sensory signaling in sensory cells; and (iv) determining changes in intracellular calcium levels in the host cell, thereby identifying the compound that modulates sensory signaling in sensory cells.

BRIEF DESCRIPTION OF THE DRAWINGS

Not applicable.

DETAILED DESCRIPTION OF THE INVENTION

I. Introduction

The present invention demonstrates, for the first time, that nucleic acids encoding phospholipase C β2 are specifically expressed in taste cells. These nucleic acids and the polypeptides that they encode are referred to as "TC-PLCβ2" for taste cell specific phospholipase C β2. These taste cell specific nucleic acids and polypeptides are components of the taste transduction pathway, and the polypeptides have the ability to catalyze the hydrolysis of phosphatidylinostol 4,5-biphosphate ($PIP_2$).

The invention thus provides methods of screening for modulators, e.g., activators, inhibitors, stimulators, enhancers, agonists, and antagonists of TC-PLCβ2. Such modulators of taste transduction are useful for pharmacological and genetic modulation of taste signaling pathways. These methods of screening can be used to identify high affinity agonists and antagonists of taste cell activity. These modulatory compounds can then be used in the food and pharmaceutical industries to customize taste. For example, modulatory compounds can be added to a food or medicine, thereby altering its taste to the subject who ingests it.

Thus, the invention provides assays for taste modulation, where TC-PLCβ2 acts as a direct or indirect reporter molecule for the effect of modulators on taste transduction. TC-PLCβ2 can be used in assays, e.g., to measure changes in ion concentration; membrane potential; current flow; ion flux; transcription; signal transduction; receptor-ligand interactions; G protein binding to receptors; binding to G protein alpha, beta and/or gamma subunits; binding to enzymes; G protein subunit ligand binding; second messenger concentrations; neurotransmitter release; in vitro, in vivo, and ex vivo. In one embodiment, TC-PLCβ2 can be used as an indirect reporter via attachment to a second reporter molecule such as green fluorescent protein (see, e.g., Mistili & Spector, *Nature Biotechnology* 15:961–964 (1997)). In another embodiment, TC-PLCβ2 is recombinantly expressed in cells with a G protein coupled receptor and optionally a promiscuous G protein or a signal transduction enzyme, and modulation of taste transduction via GPCR activity is assayed by measuring changes in intracellular $Ca^{2+}$ levels.

Methods of assaying for modulators of taste transduction include in vitro ligand binding assays using TC-PLCβ2, portions thereof, or chimeric proteins, oocyte TC-PLCβ2 expression; tissue culture cell TC-PLCβ2 expression; transcriptional activation of TC-PLCβ2; phosphorylation and dephosphorylation of GPCRs; G protein binding to GPCRs; ligand binding assays; voltage, membrane potential and conductance changes; ion flux assays; changes in intracellular second messengers such as cAMP and inositol triphosphate; changes in intracellular calcium levels; and neurotransmitter release.

These nucleic acids and proteins also provide valuable probes for the identification of taste cells, as the nucleic acids are specifically expressed in taste cells. For example, probes for TC-PLCβ2 can be used to identify subsets of taste cells such as foliate cells and circumvallate cells, or specific taste receptor cells, e.g., sweet, sour, salty, and bitter. TC-PLCβ2 polypeptides can also be used to generate monoclonal and polyclonal antibodies useful for identifying taste receptor cells, e.g., immunohistochemical assays. Taste receptor cells can also be identified using techniques such as reverse transcription and amplification of mRNA, isolation of total RNA or poly $A^+$ RNA, northern blotting, dot blotting, in situ hybridization, RNase protection, S1 digestion, high density oligonucleotide arrays, western blots, and the like. TC-PLCβ2 nucleic acids and polypeptides also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors. Finally, TC-PLCβ2s also provide useful nucleic acid probes for paternity and forensic investigations.

Functionally, TC-PLCβ2 represents a phospholipase C involved in taste transduction. The phospholipase C has the ability to catalyze the hydrolysis of phosphatidylinositol 4,5-biphosphate ($PIP_2$) and thereby generates two second messenger molecules (inositol 1,4,5-trisphosphate ($IP_3$) and diacylglycerol (DAG)) in response to the binding of various ligands to their cell surface receptors (for a description of the structure and function of phospholipase C, see, e.g., Park et al., *J. Biol. Chem.* 267(23):16048–16055 (1992)).

Structurally, the nucleotide sequence of TC-PLCβ2 (see, e.g., SEQ ID NO:3 isolated from human; see, also, SEQ ID NO:1 isolated from rat described in Example I) encodes a polypeptide of approximately 1181 amino acids with a predicted molecular weight of approximately 136 kDa and a predicted range of 131–141 kDa (see, e.g., the amino acid sequence of human PLC-β2 published in Park et al. *J. Biol Chem.* 267:16048–16055 (1992), SEQ ID NO:4; see, also, SEQ ID NO:2 isolated from rat). Related TC-PLCβ2 genes from other species share at least about 70% amino acid identity over an amino acid region at least about 25 amino acids in length, preferably 50 to 100 amino acids in length. TC-PLCβ2 is specifically expressed in circumvallate, foliate and fungiform taste receptor cells of the tongue. TC-PLCβ2 is a moderately abundant sequence found in approximately 1/5000 cDNAs from single taste receptor cells, and approximately 1/50000 cDNAs from an oligo-dT primed circumvallate cDNA library (see Example I).

The present invention also provides polymorphic variants of TC-PLCβ2 depicted in SEQ ID NO:2: variant #1, in which a threonine residue is substituted for a serine residue at amino acid position 4; variant #2, in which a leucine residue is substituted for an isoleucine residue at amino acid position 18; and variant #3, in which a lysine residue is substituted for an arginine residue at amino acid position 25.

The present invention also provides polymorphic variants of TC-PLCβ2 depicted in SEQ ID NO:4: variant #1, in which an arginine residue is substituted for a lysine residue at amino acid position 12; variant #2, in which an isoleucine residue is substituted for a leucine residue at amino acid position 131; and variant #3, in which a phenylalanine residue is substituted for a tryptophan residue at amino acid position 493.

Specific regions of the TC-PLCβ2 nucleotide and amino acid sequences may be used to identify polymorphic variants, interspecies homologs, and alleles of TC-PLCβ2. This identification can be made in vitro, e.g., under stringent hybridization conditions or with PCR and sequencing, or by using the sequence information in a computer system for comparison with other nucleotide or amino acid sequences. Typically, identification of polymorphic variants and alleles of TC-PLCβ2 is made by comparing an amino acid sequence of about 25 amino acids or more, preferably 50–100 amino acids. Amino acid identity of approximately at least 70% or above, preferably 80%, most preferably 90–95% or above typically demonstrates that a protein is a polymorphic variant, interspecies homolog, or allele of TC-PLCβ2. Sequence comparison can be performed using any of the sequence comparison algorithms discussed below. Antibodies that bind specifically to TC-PLCβ2 or a conserved region thereof can also be used to identify alleles, interspecies homologs, and polymorphic variants.

Polymorphic variants, interspecies homologs, and alleles of TC-PLCβ2 are confirmed by examining taste cell specific expression of the putative TC-PLCβ2 polypeptide. Typically, TC-PLCβ2 having the amino acid sequence of SEQ ID NOS:2 or 4 is used as a positive control, e.g., in immunoassays using antibodies directed against the amino acid sequence of SEQ ID NOS:2 or 4, in comparison to the putative TC-PLCβ2 protein to demonstrate the identification of a polymorphic variant or allele of TC-PLCβ2. Alternatively, TC-PLCβ2 having the nucleic acid sequences of SEQ ID NOS:1 or 3 is used as a positive control, e.g., in in situ hybridization with SEQ ID NOS:1 or 3, in comparison to the putative TC-PLCβ2 nucleotide sequences to demonstrate the identification of a polymorphic variant or allele of TC-PLCβ2. The polymorphic variants, alleles and interspecies homologs of TC-PLCβ2 are expected to retain the ability to catalyze the hydrolysis of phosphatidylinositol 4,5-biphosphate.

TC-PLCβ2 nucleotide and amino acid sequence information may also be used to construct models of taste cell specific polypeptides in a computer system. These models are subsequently used to identify compounds that can activate or inhibit TC-PLCβ2. Such compounds that modulate the activity of TC-PLCβ2 can be used to investigate the role of TC-PLCβ2 in taste transduction or can be used as therapeutics.

Identification of taste cell specific expression of TC-PLCβ2 provides a means for assaying for inhibitors and activators of taste cell activity. TC-PLCβ2 is useful for testing taste modulators using in vivo and in vitro expression that measure, e.g., transcriptional activation of TC-PLCβ2; ligand binding; phosphorylation and dephosphorylation; binding to G-proteins; G protein activation; regulatory molecule binding; voltage, membrane potential and conductance changes; ion flux; intracellular second messengers such as cAMP, inositol triphosphate, diacyl glycerol; intracellular calcium levels; and neurotransmitter release. Such activators and inhibitors identified using TC-PLCβ2 can be used to further study taste transduction and to identify specific taste agonists and antagonists. Such activators and inhibitors are useful as pharmaceutical and food agents for customizing taste.

Methods of detecting TC-PLCβ2 nucleic acids and expression of TC-PLCβ2 are also useful for identifying taste cells and creating topological maps of the tongue and the relation of tongue taste receptor cells to taste sensory neurons in the brain. Furthermore, these nucleic acids can be used to diagnose diseases related to taste by using assays such as northern blotting, dot blotting, in situ hybridization, RNase protection, and the like. Chromosome localization of the genes encoding human TC-PLCβ2 can also be used to identify diseases, mutations, and traits caused by and associated with TC-PLCβ2. Techniques, such as high density oligonucleotide arrays (GeneChip™), can be used to screen for mutations, polymorphic variants, alleles and interspecies homologs of TC-PLCβ2.

II. Definitions

As used herein, the following terms have the meanings ascribed to them unless specified otherwise.

"Sensory cells" are cells that are found in sensory organs or parts thereof (e.g., taste buds, retina, etc.) and that participate in sensing an external stimulus.

"Sensory cell specific" genes or proteins refer to those which are expressed exclusively, or preferentially, in the sensory cells but not in non-sensory cells.

"Taste cells" are neuroepithelial cells that are organized into groups to form taste buds of the tongue, e.g., foliate, fungiform, and circumvallate cells (see, e.g., Roper et al., Ann. Rev. Neurosci. 12:329–353 (1989)).

"Taste cell specific" genes or proteins refer to those which are expressed exclusively, or preferentially, in the taste receptor cells but not in non-taste cells, or in subsets of Gustducin positive cells.

"Taste cell specific phospholipase C" or "TC-PLCβ2" refers to a phospholipase C protein that is specifically expressed in taste cells such as foliate, fungiform, and circumvallate cells. Such taste cells can be identified because they express molecules such as Gustducin, a taste cell specific G-protein (McLaughlin et al., Nature 357:563–569 (1992)). Taste cells can also be identified on the basis of morphology (see, e.g., Roper, supra). TC-PLCβ2 encodes a phospholipase C protein with the ability to catalyze the hydrolysis of phosphatidylinostol 4,5-biphosphate ($PIP_2$) and thereby generates two second messenger molecules (inositol 1,4,5-trisphosphate ($IP_3$) and diacylglycerol (DAG)) in response to the binding of various ligands to their cell surface receptors (for description of the structure and function of phospholipase C, see, e.g., Park et al., J. Biol. Chem. 267(23):16048–16055 (1992)).

Protein "domains" such as a ligand binding domain, an active site, etc. are found in the polypeptides of the invention. Such domains are useful for making chimeric proteins and for in vitro assays of the invention. These domains can be structurally identified using methods known to those of skill in the art, such as sequence analysis programs that identify hydrophobic and hydrophilic domains (see, e.g., Kyte & Doolittle, J. Mol. Biol. 157:105–132 (1982)).

A "TC-PLCβ2 domain" refers to a ligand binding domain, a subunit association domain, an active site, etc., identified above, that has at least 70% identity to a ligand binding domain, an active site, etc., from a polypeptide having a sequence of SEQ ID NOS:2 or 4. Such domains can be used to make recombinant fusion proteins or chimeras, where a TC-PLCβ2 domain is fused to another molecule, such as a reporter molecule, e.g., Green Fluorescent Protein, β-gal, etc. Fusion proteins can also be made using a full length TC-PLCβ2 polypeptide.

The term TC-PLCβ2 therefore refers to polymorphic variants, alleles, mutants, and interspecies homologs that: (1) have about 70% amino acid sequence identity, preferably about 85–90% amino acid sequence identity to SEQ ID NOS:2 and 4 over a window of about 25 amino acids, preferably 50–100 amino acids; (2) bind to antibodies raised against an immunogen comprising an amino acid sequence of SEQ ID NOS:2 and 4 and conservatively modified variants thereof; or (3) specifically hybridize (with a size of at least about 500, preferably at least about 900 nucleotides) under stringent hybridization conditions to a sequence SEQ ID NOS:1 or 3, and conservatively modified variants thereof.

"TC-GPCR" refers to a G-protein coupled receptor that is specifically expressed in taste cells such as foliate, fungiform, and circumvallate cells (see, e.g., TR1 and TR2 in Hoon et al., Cell 96:541–551 (1999)). Such taste cells can be identified because they express molecules such as Gustducin, a taste cell specific G-protein (McLaughlin et al., Nature 357:563–569 (1992)). Taste cells can also be identified on the basis of morphology (see, e.g., Roper, supra).

TC-GPCR encodes G-protein coupled receptors with seven transmembrane regions that have "G-protein coupled receptor activity (GPCR activity)," e.g., they bind to G-proteins in response to extracellular stimuli and promote production of second messengers such as $IP_3$, cAMP, and $Ca^{2+}$ via stimulation of enzymes such as phospholipase C and adenylate cyclase (for a description of the structure and function of G-protein coupled receptors, see, e.g., Fong, supra, and Baldwin, supra).

"GPCR activity" refers to the ability of a GPCR to transduce a signal. Such activity can be measured in a heterologous cell, by coupling a GPCR (or a chimeric GPCR) to either a G protein or promiscuous G protein such as Gα15, and an enzyme such as PLC, and measuring increases in intracellular calcium (see, e.g., Offermans & Simon, J. Biol. Chem. 270:15175–15180 (1995)). Receptor activity can be effectively measured by recording ligand-induced changes in $[Ca^{2+}]_i$ using fluorescent $Ca^{2+}$-indicator dyes and fluorometric imaging. Optionally, the polypeptides of the invention are involved in sensory transduction, optionally taste transduction in taste cells.

Protein domains such as a ligand binding domain, an active site, a subunit association region, etc. are found in the polypeptides of the invention. Such domains are useful for making chimeric proteins and for in vitro assays of the invention. These domains can be structurally identified using methods known to those of skill in the art, such as sequence analysis programs that identify hydrophobic and hydrophilic domains (see, e.g., Kyte & Doolittle, J. Mol. Biol. 157:105–132 (1982)).

"Promiscuous G-protein alpha subunit" refers to a G-protein alpha subunit with the ability to form a subunit of a heterotrimeric G-protein, that has "G-protein subunit activity," e.g., has the ability to form G-proteins that bind GTP. In response to extracellular stimuli, a promiscuous G-protein couples a wide range of G-protein coupled receptors to a G-protein and appropriate signaling pathway such as PLC and $Ca^{2+}$ release. See, e.g., Offermanns & Simon, J. Biol. Chem. 270:15175–15180 (1995).

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect, amphibian, or mammalian cells such as CHO, HeLa, HEK 293 and the like.

"Biological sample" as used herein is a sample of biological tissue or fluid that contains nucleic acids or polypeptides of TC-PLCβ2. Such samples include, but are not limited to, tissue isolated from humans, mice, and rats, in particular, tongue. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Preferred tissues include tongue tissue, isolated taste buds, and testis tissue.

The phrase "functional effects" in the context of assays for testing compounds that modulate TC-PLCβ2 mediated taste transduction includes the determination of any parameter that is indirectly or directly under the influence of TC-PLCβ2, e.g., a functional, physical or chemical effect. It includes changes in ion flux, membrane potential, current flow, transcription, radiolabeled GTP binding; G-protein binding, GPCR phosphorylation or dephosphorylation, signal transduction, receptor-ligand interactions, second messenger concentrations (e.g., cAMP, $IP_3$, DAG or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of TC-PLCβ2, e.g., functional, physical or chemical effects. Such functional effects can be measured by any means known to those skilled in the art, e.g., changes in spectroscopic characteristics (e.g., fluorescence, absorbance, refractive index); hydrodynamic (e.g., shape), chromatographic, or solubility properties; voltage, membrane potential and conductance changes; ion flux or electrical activity assays (e.g., patch claming, voltage-sensitive dyes, whole cell currents, radio-isotope efflux); inducible markers; radiolabeled GPT binding; oocyte TC-PLCβ2 expression; tissue culture cell TC-PLCβ2 expression; transcriptional activation of TC-PLCβ2; ligand binding assays; changes in intracellular second messengers such as cAMP and inositol triphosphate ($IP_3$); changes in intracellular calcium levels; neurotransmitter release, and the like.

"Inhibitors," "activators," and "modulators" of TC-PLCβ2 refer to inhibitory, activating, or modulating molecules identified using in vitro and in vivo assays for taste transduction, e.g., ligands, agonists, antagonists, and their homologs and mimetics. Inhibitors are compounds that decrease, block, prevent, delay activation, inactivate, desensitize, or down regulate taste transduction, e.g., antagonists. Activators are compounds that increase, open, activate, facilitate, enhance activation, sensitize or up regulate taste transduction, e.g., agonists. Modulators include compounds that, e.g., alter the interaction of a polypeptide with: G protein coupled receptors; extracellular proteins that bind activators or inhibitor (e.g., ebnerin and other members of hydrophobic carrier family); G proteins; G protein alpha, beta and/or gamma subunits; kinases (e.g., homologs of rhodopsin kinase and beta adrenergic receptor kinases that are involved in deactivation and desensitization of a receptor); and arrestin-like proteins, which also deactivate and desensitize receeptors, $PIP_2$, etc. Modulators include genetically modified versions of TC-PLCβ2, e.g., with altered activity, as well as naturally occurring and synthetic ligands, antagonists, agonists, small chemical molecules and the like. Such assays for inhibitors and activators include, e.g., expressing TC-PLCβ2 in vitro, in cells, or cell membranes, applying putative modulator compounds, and then determining functional effects on taste transduction, as described above.

Samples or assays comprising TC-PLCβ2 that are treated with a potential activator, inhibitor, or modulator are compared to control samples without the inhibitor, activator, or modulator to examine the extent of inhibition. Control samples (untreated with inhibitors) are assigned a relative TC-PLCβ2 activity value of 100%. Inhibition of TC-PLCβ2 is achieved when the TC-PLCβ2 activity value relative to the control is about 80%, optionally 50% or 25–0%. Activation of TC-PLCβ2 is achieved when the TC-PLCβ2 activity value relative to the control (untreated with activators) is 110%, optionally 150%, 200–500%, or 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated TC-PLCβ2 nucleic acid is separated from open reading frames that flank the TC-PLCβ2 gene and encode proteins other than TC-PLCβ2. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an carbon that is bound to a hydrogen, a carboxyl group, an amino group, and an R group. Examples of amino acid analogs include homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes (A, T, G, C, U, etc.).

"Conservatively modified variants" applies to both amino acid and nucleic acid sequences. With respect to particular nucleic acid sequences, conservatively modified variants refers to those nucleic acids which encode identical or essentially identical amino acid sequences, or, where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 80% identity, preferably 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length. In most preferred embodiments, the sequences are substantially identical over the entire length of, e.g., the coding region.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see *Fundamental Immunology* (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv), or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348, 552–554 (1990); Marks et al., *Biotechnology* 10, 779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-TC-PLCβ2" antibody is an antibody or antibody fragment that specifically binds a polypeptide encoded by the TC-PLCβ2 gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to TC-PLCβ2 from specific species such as rat, mouse, or human can be selected to obtain only those polyclonal antibodies that are specifically immunoreactive with TC-PLCβ2 and not with other proteins, except for polymorphic variants and alleles of TC-PLCβ2. This selection may be achieved by subtracting out antibodies that cross-react with TC-PLCβ2 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

III. Assays for Taste Modulation

A. Assays for taste cell specific phospholipase C activity

TC-PLCβ2 and its alleles, interspecies homologs, and polymorphic variants participate in taste transduction. The activity of TC-PLCβ2 polypeptides (encoded by, e.g., SEQ ID NOS:1 or 3), domains, or chimeras thereof can be assessed using a variety of in vitro and in vivo assays that measure functional, chemical and physical effects, e.g., measuring ligand binding (e.g., radioactive ligand), measuring second messenger (e.g., cAMP, cGMP, IP$_3$, DAG, or Ca$^{2+}$), ion flux or electrical activity, phosphorylation levels, transcription levels, neurotransmitter levels, and the like. Furthermore, such assays can be used to screen for activators, inhibitors, and modulators of TC-PLCβ2. Modulators can also be genetically modified versions of TC-PLCβ2. Such activators, inhibitors, and modulators of taste transduction activity are useful for customizing taste.

The TC-PLCβ2 of the assay will be selected from a polypeptide having a sequence of SEQ ID NOS:2 or 4 or conservatively modified variant thereof. Alternatively, the TC-PLCβ2 of the assay will be derived from a eukaryote and include an amino acid subsequence having at least about 70% amino acid sequence identity SEQ ID NOS:2 or 4. Generally, the amino acid sequence identity will be at least 70%, optionally at least 75%, 80%, 85%, optionally at least 90–95%. Optionally, the polypeptide of the assays will comprise a domain of TC-PLCβ2, such as a ligand binding domain, G protein association domain, active site, and the like. Either TC-PLCβ2 or a domain thereof can be covalently linked to a heterologous protein to create a chimeric protein used in the assays described herein.

Modulators of TC-PLCβ2 activity are tested using TC-PLCβ2 polypeptides, as described above, either recombinant or naturally occurring. The protein can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation is tested using one of the in vitro or in vivo assays described herein. Taste transduction can also be examined in vitro with soluble or solid state reactions, using a chimeric molecule, comprising, e.g., a ligand binding domain of TC-PLCβ2, or a domain of TC-PLCβ2, or a full-length TC-PLCβ2. Furthermore, ligand-binding domains of the protein of interest can be used in vitro in soluble or solid state reactions to assay for ligand binding.

The effects of the test compounds upon the function of the polypeptides can be measured by examining any of the parameters described above. Any suitable physiological change that affects TC-PLCβ2 activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as cAMP, cGMP, IP$_3$, DAG, or Ca$^{2+}$.

Samples or assays that are treated with a test compound which potentially activates, inhibits, or modulates TC-PLCβ2 are compared to control samples that are not treated without the test compound, to examine the extent of modulation. Control samples (untreated with activators, inhibitors, or modulators) are assigned a relative TC-PLCβ2 activity value of 100%. Inhibition of TC-PLCβ2 is achieved when the TC-PLCβ2 activity value relative to the control is about 90% (e.g., 10% less than the control), optionally 50%, or 25–0%. Activation of TC-PLCβ2 is achieved when the TC-PLCβ2 activity value relative to the control is 110% (e.g., 10% more than the control), optionally 150%, 200–500%, or 1000–2000%.

In one embodiment, ligand binding to TC-PLCβ2, a domain thereof, or chimeric protein comprising TC-PLCβ2 or a domain thereof can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties. In one example, radiolabeled GTP is used.

In another embodiment, receptor-G protein interactions are examined. For example, binding of a G protein to a receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. For example, an activator can be added to the receptor and G protein in the absence, thereby forming a tight complex of a G protein, and then an inhibitor can be screened by looking at dissociation of the receptor-G protein complex. In the presence of GTP, release of the alpha subunit of the G protein from the other two G protein subunits serves as a criterion of activation.

In another example, activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G proteins. The kinase/arrestin pathway plays a key role in the desensitization of many GPCR receptors. For example, compounds that modulate the duration of a taste receptor being active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., *Nature* 348:125–32 (1990); Pitcher et al., *Annu. Rev. Biochem.* 67:653–92 (1998).

In another embodiment, signal transduction enzymes and second messengers are examined. An activated or inhibited G protein will in turn alter the properties of target enzymes, channels, and other effector proteins. The classic examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol (DAG) and $IP_3$ by phospholipase C, and in turn, for calcium mobilization by $IP_3$.

Signal transduction typically initiates subsequent intracellular events via, e.g., G-proteins and/or other enzymes, such as adenylate cyclase or phospholipase C, which are downstream from the G-proteins in taste transduction pathways. For example, receptor activation may result in a change in the level of intracellular cyclic nucleotides, e.g., cAMP or cGMP, by activating or inhibiting enzymes such as adenylate cyclase by G-protein α and βγ subunits. These intracellular cyclic nucleotides, in turn, may modulate other molecules, such as cyclic nucleotide-gated ion channels, e.g., channels that are made permeable to cations upon activation by binding of cAMP or cGMP (see, e.g., Altenhofen et al., *Proc. Natl. Acad. Sci. U.S.A.* 88:9868–9872 (1991) and Dhallan et al., *Nature* 347:184–187 (1990)). Cells for this type of assay can be made by co-transfection of a host cell with any one or a combination of DNA encoding a cyclic nucleotide-gated ion channel, GPCR phosphatase, DNA encoding TC-PLCβ2, and DNA encoding a G-protein coupled receptor. The receptor may be, e.g., metabotropic glutamate receptors, muscarinic acetylcholine receptors, dopamine receptors, serotonin receptors, and the like, which, when activated, causes a change in cyclic nucleotide levels in the cytoplasm.

In response to external stimuli, certain G-protein coupled receptors may activate other effectors, such as phospholipase C, through G-proteins. Activation of phospholipase C results in the production of inositol 1,4,5-triphosphate ($IP_3$) and diacylglycerol (DAG) from inositol 4,5-biphosphate (PIP2) (see, e.g., Berridge & Irvine, *Nature* 312:315–21 (1984)). $IP_3$ in turn stimulates the release of intracellular calcium ion stores. Cells may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Thus, a change in the level of second messengers, such as $IP_3$, DAG, or $Ca^{2+}$ can be used to assess TC-PLCβ2 function. Furthermore, a change in the level of these second messengers can be used to screen for activators, inhibitors, and modulators of TC-PLCβ2 polypeptides.

For example, the activity of TC-PLCβ2 polypeptides can be assessed by measuring, e.g., changes in intracellular second messengers, such as cAMP, cGMP, $IP_3$, DAG, or $Ca^{2+}$. Therefore, the second messenger levels can be used as reporters for detecting potential activators, inhibitors, and modulators of TC-PLCβ2 polypeptides.

In one embodiment, the changes in intracellular cAMP or cGMP can be measured using immunoassays. The method described in Offermanns & Simon, *J. Biol. Chem.* 270:15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^{3}H$-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, intracellular $Ca^{2+}$ levels can be analyzed, e.g., using fluorescent $Ca^{2+}$ indicator dyes and fluorometric imaging (see, e.g., Hall et al., *Nature* 331:729

(1988); Kudo et al., *Neuros.* 50:619–625 (1992); van Heugten et al., *J. Mol. Cell. Cardiol.* 26:1081–93 (1994)).

In another embodiment, the activity of TC-PLCβ2 can also be assessed by measuring changes in ion flux or electrical activity of cells or cell membranes. Changes in ion flux may be measured by determining changes in polarization (i.e., electrical potential) of the cell or membrane expressing TC-PLCβ2. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981)). Other known assays include: radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al., *J. Membrane Biology* 137:59–70 (1994)). A method for the whole-cell recording from non-dissociated taste cells within mouse taste bud is described in Miyamoto et al., *J. Neurosci Methods* 64:245–252 (1996). Therefore, changes in ion flux can be used to screen for activators, inhibitors, and modulators of TC-PLCβ2. Generally, the compounds to be tested are present in the range from 1 pM to 100 mM.

Assays for measuring changes in ion flux include cells that are loaded with ion or voltage sensitive dyes to report TC-PLCβ2 activity. Assays for determining activity of these polypeptides can also use known agonists and antagonists for these polypeptides as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog.

In another embodiment, phosphorylation of taste cell specific proteins can be measured to assess the effects of a test compound on TC-PLCβ2 function. This can be achieved by using a method disclosed in, e.g., U.S. Pat. No. 5,834,216, herein incorporated by reference. A duplicate cell culture containing expressed TC-PLCβ2 can be prepared. One of the duplicate cultures is exposed to a test compound. Cell lysates from the duplicate cultures are prepared. The cell lysates are contacted with ATP wherein the ATP has a gamma-phosphate having a detectable label, or an analog of a gamma phosphate (i.e., having a label capable of being transferred to a phosphorylation site such as gamma $S^{35}$). The level of phosphorylated taste cell specific proteins may be measured by precipitating the cell lysates with an antibody specific for taste cell specific proteins. After precipitation, phosphorylated (labeled) taste cell specific proteins may be separated from other cellular proteins by electrophoresis or by chromatographic methods. By way of example, labeled taste cell specific proteins may be separated on denaturing polyacrylamide gels after which the separated proteins may be transferred to, for example, a nylon or nitrocellulose membrane followed by exposure to X-ray film. Relative levels of phosphorylation are then determined after developing the exposed X-ray film and quantifying the density of bands corresponding to the taste cell specific proteins, for example, densitometry. The autoradiograph may also be used to localize the bands on the membrane corresponding to labeled taste cell specific proteins after which they may be excised from the membrane and counted by liquid scintillation or other counting methods. Using this method, a test compound which effects the function of TC-PLCβ2 is identified by its ability to increase or decrease phosphorylation of taste cell specific proteins compared to control cells not exposed to the test compound.

In another embodiment, transcription levels can be measured to assess the effects of a test compound on TC-PLCβ2 function. A host cell containing TC-PLCβ2 is contacted with a test compound for a sufficient time to effect any interactions, and then the level of TC-PLCβ2 gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of TC-PLCβ2 may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, TC-PLCβ2 can be used as indirect reporters via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks TC-PLCβ2. A substantially identical cell may be derived from the same cells from which the recombinant cell was prepared but which had not been modified by introduction of heterologous DNA. Any difference in the amount of transcription indicates that the test compound has in some manner altered the activity of TC-PLCβ2.

Other physiological change that affects TC-PLCβ2 activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and the like.

In a preferred preferred embodiment, TC-PLCβ2 activity is measured by expressing TC-PLCβ2 in a heterologous cell with a taste cell specific G-protein receptor (TC-GPCR; see U.S. Ser. No. 09/361,651 filed Jul. 27, 1999, U.S. Ser. No. 09/361,631 filed Jul. 27, 1998, and U.S. Ser. No. 60/112,747 filed Dec. 17, 1998) and a promiscuous G-protein that links the receptor to a phospholipase C signal transduction pathway (see Offermanns & Simon, *J. Biol. Chem.* 270:15175–15180 (1995); see also Example III). A TC-GPCR, such as GPCR-B3 or GPCR-B4, can be used in the assays. Gα14 or Gα15 can be used as a promiscuous G-protein alpha subunit (Wilkie et al., *PNAS USA* 88:10049–10053 (1991)). Such promiscuous G-proteins allow coupling of a wide range of receptors. Alternatively, a taste cell specific G-protein alpha subunit can be used, such as the Gα subunit described in copending patent application U.S. Ser. No. 60/117,367 (TTC ref. no. 02307E-092600)

filed Jan. 27, 1999, herein incorporated by reference. Preferably the cell line is HEK-293 (which does not naturally express GPCR-B4) and the promiscuous G-protein is Gα15 (Offermanns & Simon, supra). Modulation of taste transduction is assayed by measuring changes in intracellular $Ca^{2+}$ levels, which change in response to modulation of the TC-PLCβ2 signal transduction pathway via administration of a molecule that associates with TC-PLCβ2. Changes in $Ca^{2+}$ levels are preferably measured using fluorescent $Ca^{2+}$ indicator dyes and fluorometric imaging.

B. Modulators

The compounds tested as modulators of TC-PLCβ2 can be any small chemical compound, or a biological entity, such as a protein, sugar, nucleic acid or lipid. Alternatively, modulators can be genetically altered versions of TC-PLC2. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309–314 (1996) and PCT/US96/10287), carbohydrate libraries (see, e.g., Liang et al., *Science,* 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provide soluble assays using molecules such as a domain such as ligand binding domain, an active site, a subunit association region, etc.; a domain that is covalently linked to a heterologous protein to create a chimeric molecule; TC-PLCβ2; a cell or tissue expressing TC-PLCβ2, either naturally occurring or recombinant. In another embodiment, the invention provides solid phase based in vitro assays in a high throughput format, where the domain, chimeric molecule, TC-PLCβ2, or cell or tissue expressing TC-PLCβ2 is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000–20,000 different compounds is possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:6031–6040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-based Assays

Yet another assay for compounds that modulate TC-PLCβ2 activity involves computer assisted drug design, in which a computer system is used to generate a three-dimensional structure of TC-PLCβ2 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering G-protein amino acid sequences of at least 10 amino acid residues or corresponding nucleic acid sequences encoding a TC-PLCβ2 polypeptide into the computer system. The amino acid sequence of the polypeptide or the nucleic acid encoding the polypeptide is selected from SEQ ID NOS:2 or 4, or SEQ ID NOS:1 or 3, or conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art. The three-dimensional structural model of the protein can be saved to a computer readable form and be used for further analysis (e.g., identifying potential ligand binding regions of the protein and screening for mutations, alleles and interspecies homologs of the gene).

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the TC-PLCβ2 protein to identify ligands that bind to TC-PLCβ2. Binding affinity between the protein and ligands is determined using energy terms to determine which ligands have an enhanced probability of binding to the protein. The results, such as three-dimensional structures for potential ligands and binding affinity of ligands, can also be saved to a computer readable form and can be used for further analysis (e.g., generating a three dimensional model of mutated proteins having an altered binding affinity for a ligand).

Computer systems are also used to screen for mutations, polymorphic variants, alleles and interspecies homologs of TC-PLCβ2 genes. Such mutations can be associated with disease states or genetic traits. As described above, high density oligonucleotide arrays (GeneChip™) and related technology can also be used to screen for mutations, polymorphic variants, alleles and interspecies homologs. Once the variants are identified, diagnostic assays can be used to identify patients having such mutated genes. Identification of the mutated TC-PLCβ2 genes involves receiving input of a first nucleic acid or amino acid sequence encoding TC-PLCβ2 selected from the group consisting of SEQ ID NOS:1 or 3, or SEQ ID NOS:2 or 4, and conservatively modified versions thereof. The sequence is entered into the computer system as described above and then saved to a computer readable form. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in TC-PLCβ2 genes, and mutations associated with disease states and genetic traits.

IV. Isolation of the Nucleic Acid Encoding TC-PLCβ2

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding TC-PLCβ2

In general, the nucleic acid sequences encoding TC-PLCβ2 and related nucleic acid sequence homologs are cloned from cDNA and genomic DNA libraries by hybridization with a probe, or isolated using amplification techniques with oligonucleotide primers. For example, TC-PLCβ2 sequences are typically isolated from mammalian nucleic acid (genomic or cDNA) libraries by hybridizing with a nucleic acid probe, the sequence of which can be derived from SEQ ID NOS:1 or 3. A suitable tissue from which TC-PLCβ2 and cDNA can be isolated is tongue tissue, preferably taste bud tissue, more preferably individual taste cells. For example, circumvallate, foliate, fungiform taste receptor cells can be used to isolate TC-PLCβ2 RNA and cDNA.

Amplification techniques using primers can also be used to amplify and isolate TC-PLCβ2 from DNA or RNA (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length TC-PLCβ2.

Nucleic acids encoding TC-PLCβ2 can also be isolated from expression libraries using antibodies as probes. Such polyclonal or monoclonal antibodies can be raised using the sequence of SEQ ID NOS:2 or 4.

TC-PLCβ2 polymorphic variants, alleles, and interspecies homologs that are substantially identical to TC-PLCβ2 can be isolated using TC-PLCβ2 nucleic acid probes and oligonucleotides under stringent hybridization conditions, by screening libraries. Alternatively, expression libraries can be used to clone TC-PLCβ2 and its polymorphic variants, alleles, and interspecies homologs, by detecting expressed homologs immunologically with antisera or purified antibodies made against TC-PLCβ2 which also recognize and selectively bind to the TC-PLCβ2 homolog.

To make a cDNA library, one should choose a source that is rich in TC-PLCβ2 mRNA, e.g., tongue tissue, or isolated taste buds. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.,* 72:3961–3965 (1975).

An alternative method of isolating TC-PLCβ2 nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of TC-PLCβ2 directly from mRNA, from cDNA, from genomic libraries or cDNA libraries. Degenerate oligonucleotides can be designed to amplify TC-PLCβ2 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of TC-PLCβ2 encoding mRNA in physiological samples, for nucleic acid sequencing, or for other purposes. Genes amplified by the PCR reaction can be purified from agarose gels and cloned into an appropriate vector.

Gene expression of TC-PLCβ2 can also be analyzed by techniques known in the art, e.g., reverse transcription and amplification of mRNA, isolation of total RNA or poly A$^+$ RNA, northern blotting, dot blotting, in situ hybridization, RNase protection, and the like. In one embodiment, high density oligonucleotide arrays technology (e.g., GeneChip™) is used to identify homologs and polymorphic variants of the TC-PLCβ2 of the invention (see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998)).

Synthetic oligonucleotides can be used to construct recombinant TC-PLCβ2 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the TC-PLCβ2 nucleic acid. The specific subsequence is then ligated into an expression vector.

The nucleic acid encoding TC-PLCβ2 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene or nucleic acid, such as those cDNAs encoding TC-PLCβ2, one typically subclones TC-PLCβ2 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the TC-PLCβ2 proteins are available in, e.g., *E. coli*, Bacillus sp., and Salmonella (Palva et al., *Gene* 22:229–235 (1983); Mosbach et al., *Nature* 302:543–545 (1983)). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the TC-PLCβ2 encoding nucleic acid in host cells. A typical expression cassette thus contains a promoter operably linked to the nucleic acid sequence encoding TC-PLCβ2 and signals required for efficient polyadenylation of the transcript, ribosome binding sites, and translation termination. The nucleic acid sequence encoding TC-PLCβ2 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a TC-PLCβ2 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of TC-PLCβ2, which are then purified using standard techniques (see, e.g., Colley et al., *J. Biol. Chem.* 264:17619–17622 (1989); *Guide to Protein Purification*, in

*Methods in Enzymology,* vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983)).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing TC-PLCβ2.

After the expression vector is introduced into the cells, the transfected cells are cultured under conditions favoring expression of TC-PLCβ2, which is recovered from the culture using standard techniques identified below.

V. Purification of TC-PLCβ2

Either naturally occurring or recombinant TC-PLCβ2 can be purified for use in functional assays. Preferably, recombinant TC-PLCβ2 is purified. Naturally occurring TC-PLCβ2 is purified, e.g., from mammalian tissue such as tongue tissue, and any other source of a TC-PLCβ2 homolog. Recombinant TC-PLCβ2 is purified from any suitable expression system.

TC-PLCβ2 may be purified to substantial purity by standard techniques, including selective precipitation with such substances as ammonium sulfate; column chromatography, immunopurification methods, and others (see, e.g., Scopes, *Protein Purification: Principles and Practie* (1982); U.S. Pat. No. 4,673,641; Ausubel et al., supra; and Sambrook et al., supra).

A number of procedures can be employed when recombinant TC-PLCβ2 is being purified. For example, proteins having established molecular adhesion properties can be reversible fused to TC-PLCβ2. With the appropriate ligand, TC-PLCβ2 can be selectively adsorbed to a purification column and then freed from the column in a relatively pure form. The fused protein is then removed by enzymatic activity. Finally TC-PLCβ2 could be purified using immunoaffinity columns.

A. Purification of TC-PLCβ2from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of TC-PLCβ2 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forminG-proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. TC-PLCβ2 is separated from other bacterial proteins by standard separation techniques, e.g., with Ni-NTA agarose resin.

Alternatively, it is possible to purify TC-PLCβ2 from bacteria periplasm. After lysis of the bacteria, when TC-PLCβ2 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying TC-PLCβ2

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of TC-PLCβ2 can be used to isolate them from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

TC-PLCβ2 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

VI. Immunological Detection of TC-PLCβ2

In addition to the detection of TC-PLCβ2 genes and gene expression using nucleic acid hybridization technology, one can also use immunoassays to detect TC-PLCβ2, e.g., to identify taste receptor cells and variants of TC-PLCβ2. Immunoassays can be used to qualitatively or quantitatively analyze TC-PLCβ2. A general overview of the applicable technology can be found in Harlow & Lane, *Antibodies: A Laboratory Manual* (1988).

A. Antibodies to TC-PLCβ2

Methods of producing polyclonal and monoclonal antibodies that react specifically with TC-PLCβ2 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of TC-PLCβ2 comprising immunogens may be used to produce antibodies specifically reactive with TC-PLCβ2. For example, recombinant TC-PLCβ2 or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring-protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to TC-PLCβ2. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-TC-PLCβ2 proteins or even other related proteins from other organisms, using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better.

Once TC-PLCβ2 specific antibodies are available, TC-PLCβ2 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

TC-PLCβ2 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also, *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the TC-PLCβ2 or antigenic subsequence thereof). The antibody (e.g., anti-TC-PLCβ2) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide of TC-PLCβ2 or a labeled anti-TC-PLCβ2 antibody. Alternatively, the labeling agent may be a third moiety, such a secondary antibody, that specifically binds to the antibody/TC-PLCβ2 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406

(1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting TC-PLCβ2 in samples may be either competitive or noncompetitive. Noncompetitive immunoassays are assays in which the amount of antigen is directly measured. In one preferred "sandwich" assay, for example, the anti-TC-PLCβ2 antibodies can be bound directly to a solid substrate on which they are immobilized. These immobilized antibodies then capture TC-PLCβ2 present in the test sample. TC-PLCβ2 is thus immobilized is then bound by a labeling agent, such as a second TC-PLCβ2 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of TC-PLCβ2 present in the sample is measured indirectly by measuring the amount of a known, added (exogenous) TC-PLCβ2 displaced (competed away) from an anti- TC-PLCβ2 antibody by the unknown TC-PLCβ2 present in a sample. In one competitive assay, a known amount of TC-PLCβ2 is added to a sample and the sample is then contacted with an antibody that specifically binds to TC-PLCβ2. The amount of exogenous TC-PLCβ2 bound to the antibody is inversely proportional to the concentration of TC-PLCβ2 present in the sample. In a particularly preferred embodiment, the antibody is immobilized on a solid substrate. The amount of TC-PLCβ2 bound to the antibody may be determined either by measuring the amount of TC-PLCβ2 present in a TC-PLCβ2/antibody complex, or alternatively by measuring the amount of remaining uncomplexed protein. The amount of TC-PLCβ2 may be detected by providing a labeled TC-PLCβ2 molecule.

A hapten inhibition assay is another preferred competitive assay. In this assay the known TC-PLCβ2 is immobilized on a solid substrate. A known amount of anti-TC-PLCβ2 antibody is added to the sample, and the sample is then contacted with the immobilized TC-PLCp2. The amount of anti-TC-PLCβ2 antibody bound to the known immobilized TC-PLCβ2 is inversely proportional to the amount of TC-PLCβ2 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, a protein at least partially encoded by SEQ ID NOS:1 or 3 can be immobilized to a solid support. Proteins (e.g., TC-PLCβ2 proteins and homologs) are added to the assay that compete for binding of the antisera to the immobilized antigen. The ability of the added proteins to compete for binding of the antisera to the immobilized protein is compared to the ability of TC-PLCβ2 encoded by SEQ ID NOS:1 or 3 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of TC-PLCβ2 to the immunogen protein (i.e., TC-PLCβ2 of SEQ ID NOS:2 or 4). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NOS:1 or 3 that is required to inhibit 50% of binding, then the second protein is said to specifically bind to the polyclonal antibodies generated to a TC-PLCβ2 immunogen.

Other Assay Formats

Western blot (immunoblot) analysis is used to detect and quantify the presence of TC-PLCβ2 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind TC-PLCβ2. The anti-TC-PLCβ2 antibodies specifically bind to the TC-PLCβ2 on the solid support. These antibodies may be directly labeled or alternatively may be subsequently detected using labeled antibodies (e.g., labeled sheep anti-mouse antibodies) that specifically bind to the anti-TC-PLCβ2 antibodies.

Other assay formats include liposome immunoassays (LIA), which use liposomes designed to bind specific molecules (e.g.; antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize TC-PLCβ2, or secondary antibodies that recognize anti-TC-PLCβ2.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VII. Kits

TC-PLCβ2 and its homologs are a useful tool for identifying taste receptor cells, for forensics and paternity determinations, and for examining taste transduction (e.g., generating a topographical map between the taste cells of the tongue and the corresponding taste centers in the brain). Specific reagents that specifically hybridize to TC-PLCβ2 nucleic acid, such as their probes and primers, and specific reagents that specifically bind to the TC-PLCβ2 protein, e.g., their antibodies are used to examine taste cell expression and taste transduction regulation.

Nucleic acid assays for the presence of TC-PLCβ2 DNA and RNA in a sample include numerous techniques are known to those skilled in the art, such as Southern analysis, northern analysis, dot blots, RNase protection, high density oligonucleotide arrays, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis (see Example I). The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, TC-PLCβ2 protein can be detected with the various immunoassay techniques described above. The test sample is typically compared to both a positive control (e.g., a sample expressing recombinant TC-PLCβ2) and a negative control.

The present invention also provides for kits for screening for modulators of TC-PLCβ2. Such kits can be prepared from readily available materials and reagents. For example, such kits can comprise any one or more of the following materials: TC-PLCβ2, reaction tubes, and instructions for testing TC-PLCβ2 activity. Preferably, the kit contains biologically active TC-PLCβ2. Furthermore, the kit may include a label or written instructions for use of one or more of these reagents and materials in any of the assays described herein. A wide variety of kits and components can be prepared according to the present invention, depending upon the intended user of the kit and the particular needs of the user.

VIII. Administration and Pharmaceutical Compositions

Taste modulators can be administered directly to the mammalian subject for modulation of taste in vivo. Administration is by any of the routes normally used for introducing a modulator compound into ultimate contact with the tissue to be treated, preferably the tongue or mouth. The taste modulators are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The taste modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Preferably, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the LD-50 of the modulator, and the side-effects of the inhibitor at various concentrations, as applied to the mass and overall health of the subject. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Taste Cell Specific Expression of TC-PLCβ2 and Cloning cDNA libraries made from rat circumvallate single cells were used to isolate the TC-PLCβ2 nucleic acids of the invention.

Single taste receptor cells were isolated from dissociated circumvallate papillae from the rat tongue. 250 single cell cDNA libraries were generated from individual cells isolated from 20 rat papillae (in batches of 20 each) (see, e.g., Bernhardt et al., *J. Physiol.* 490:325–336 (1996); Dulac & Axel, *Cell* 83:195–206 (1995)). Amplified single cell cDNA was Southern and dot-blotted and probed with radiolabeled probes to identify potentially similar cell types. Gustducin, a G-protein specifically expressed in a subset of taste receptor cells was chosen as a marker for taste cells (McLaughlin et al., *Nature* 357:563–569 (1992)). Tubulin and N-Cam were chosen to confirm the integrity of the cells and validate the amplification reactions. Bacteriophage lambda cDNA libraries were then constructed from individual Gustducin positive cells and were plated at low density on LB/Agar plates. Seven Gustducin positive cells were obtained from 250 single cell cDNA preparations.

For differential screens, replica filter lifts were produced from all Gustducin positive cell-libraries, and from a number of Gustducin negative cell-derived libraries. The libraries were hybridized with radiolabeled cDNA from each of the Gustducin positive cells, and from bona fide non-taste cells. Clones expressed exclusively, or preferentially, in the taste receptor cells but not in non-taste cells, or in subsets of Gustducin positive cells were isolated. The novel nucleic acids were also used for in situ hybridization to tongue tissue sections to demonstrate taste cell specific expression. Clone 165-170 was chosen for further characterization, including full length cDNA isolation and sequencing. Clone 165-170 was identified as a phospholipase C β2, a signaling molecule intimately involved in G protein-coupled signaling pathways. While this gene had been previously identified, its restricted expression in subsets of taste receptor cells, and its role in taste transduction represent novel discoveries.

Clone 165-170 represents a mRNA specifically expressed in circumvallate, foliate and fungiform taste receptor cells of the tongue. This is a moderately abundant sequence found in approximately 1/5000 cDNAs from single taste receptor cells, and approximately 1/50000 cDNAs from an oligo-dT primed circumvallate cDNA library. The nucleotide sequence of clone 165-170 is shown below, as SEQ ID NO:1. In situ hybridization of clone 165-170 to tissue section demonstrates taste cell specificity. Clone 165-170 encodes a PLCβ2 isoform. This isoform was previously reported to be expressed primarily in hematopoietic cells (Park et al., *J. Biol. Chem.* 267:16048–16055 (1992)), and to be activated by the Gα subunits of the Gq class and by the βγ subunits generated by a number of different heterotrimeric G-proteins (Jian et a., *PNAS USA* 94:7971–7975 (1997)).

Example II

Expression of TC-PLCβ2 in a Heterolologous Cell with a Promiscuous G-protein a Subunit and a Taste Cell Specific G-protein Coupled Receptor TC-PLCβ2 can be expressed in a heterologous cell with a promiscuous G-protein α subunit and a taste cell specific G-protein coupled receptor to screen for activators, inhibitors, and modulators of TC-PLCβ2. A TC-GPCR, such as GPCR-B3 or GPCR-B4, can be used in the assays (see U.S. Ser. No. 60/094,465 filed Jul. 28, 1998 for the description of GPCR-B3 and U.S. Ser. No. 60/095,464 filed Jul. 28, 1998 and U.S. Ser. No. 60/112,747 filed Dec. 17, 1998 for the description of GPCR-B4). Gα14 or Gα15 can be used as a promiscuous G-protein alpha subunit (Wilkie et al., *PNAS USA* 88:10049–10053 (1991)). Such promiscuous G-proteins allow coupling of a wide range of receptors. Preferably the cell line is HEK-293 (which does not naturally express GPCR-B4) and the promiscuous G-protein is Gα15 (Offermanns & Simon, supra). Modulation of taste transduction is assayed by measuring changes in intracellular $Ca^{2+}$ levels, which change in response to modulation of the TC-PLCβ2 signal transduction pathway via administration of a molecule that associates with TC-PLCβ2. Changes in $Ca^{2+}$ levels are preferably measured using fluorescent $Ca^{2+}$ indicator dyes and fluorometric imaging. The amount of $[Ca^{2+}]_i$ is then compared to the amount of $[Ca^{2+}]_i$ in either the same cell in the absence of the test compound, or it may be compared to the amount of $[Ca^{2+}]_i$ in a substantially identical cell that lacks TC-PLCβ2.

What is claimed is:

1. A method for identifying a compound that modulates sensory signaling in taste cells, the method comprising the steps of:

(i) contacting a cell which expresses a taste cell specific phospholipase C and a taste cell specific G protein coupled receptor with the compound, wherein the phospholipase C comprises an amino acid sequence of SEQ ID NO:2 or SEQ ID NO:4; and (ii) determining the functional effect of the compound upon the cell expressing the phospholipase C and the taste cell specific G protein coupled receptor.

2. The method of claim 1, wherein the functional effect is determined by measuring concentration changes in intracellular cAMP, cGMP, $IP_3$, DAG, or $Ca^{2+}$.

3. The method of claim 2, wherein the functional effect is determined by measuring changes in the level of $IP_3$.

4. The method of claim 2, wherein the functional effect is determined by measuring concentration changes in intracellular $Ca^{2+}$.

5. The method of claim 1, wherein the cell is a eukaryotic cell.

6. The method of claim 1, wherein the phospholipase C is recombinant.

* * * * *